US00PP21630P2

(12) United States Plant Patent
Kempen

(10) Patent No.: US PP21,630 P2
(45) Date of Patent: Jan. 11, 2011

(54) ***ECHINACEA* PLANT NAMED 'POLAR BREEZE'**

(50) Latin Name: *Echinacea purpurea*
Varietal Denomination: Polar Breeze

(75) Inventor: Anthonius Johannes Maria Kempen, Mijdrecht (NL)

(73) Assignee: Gootjes-Allplant B.V., Heerhugowaard (NL)

( * ) Notice: Subject to any disclaimer, the term of this patent is extended or adjusted under 35 U.S.C. 154(b) by 0 days.

(21) Appl. No.: 12/590,822

(22) Filed: Nov. 14, 2009

(51) Int. Cl.
*A01H 5/00* (2006.01)

(52) U.S. Cl. ..... Plt./428

(58) Field of Classification Search ..... Plt./428
See application file for complete search history.

*Primary Examiner*—Kent L Bell
(74) *Attorney, Agent, or Firm*—C. A. Whealy

(57) ABSTRACT

A new and distinct cultivar of *Echinacea* plant named 'Polar Breeze', characterized by its upright and compact plant habit; strong and thick flowering stems; freely branching habit; and numerous inflorescences with white-colored ray florets.

1 Drawing Sheet

Botanical designation: *Echinacea purpurea.*
Cultivar denomination: 'POLAR BREEZE'.

BACKGROUND OF THE INVENTION

The present invention relates to a new and distinct cultivar of *Echinacea* plant, botanically known as *Echinacea purpurea,* and hereinafter referred to by the name 'Polar Breeze'.

The new *Echinacea* plant is a naturally-occurring whole plant mutation of *Echinacea purpurea* 'Mistral', disclosed in U.S. Plant Pat. No. 20,498. The new *Echinacea* was discovered by the Inventor as a single flowering plant from within a population of plants of 'Mistral' in a controlled greenhouse environment in Mijdrecht, The Netherlands on Jun. 24, 2009.

Asexual reproduction of the new *Echinacea* plant by micropropagation in a controlled greenhouse environment in Heerhugowaard, The Netherlands since Aug. 17, 2009, has shown that the unique features of this new *Echinacea* plant are stable and reproduced true to type in successive generations.

SUMMARY OF THE INVENTION

Plants of the new *Echinacea* have been observed under all possible environmental conditions. The phenotype may vary somewhat with variations in environment such as temperature and light intensity, without, however, any variance in genotype.

The following traits have been repeatedly observed and are determined to be the unique characteristics of 'Polar Breeze'. These characteristics in combination distinguish 'Polar Breeze' as a new and distinct cultivar of *Echinacea:*

1. Upright and compact plant habit.
2. Strong and thick flowering stems.
3. Freely branching habit.
4. Numerous inflorescences with white-colored ray florets.

Plants of the new *Echinacea* plant can be compared to plants of the parent, 'Mistral'. Plants of the new *Echinacea* plant differ from plants of 'Mistral' primarily in ray floret color as plants of 'Mistral' have pink-colored ray florets.

Plants of the new *Echinacea* can be compared to plants of *Echinacea purpurea* 'Kim's Knee High', disclosed in U.S. Plant Pat. No. 12,242. In side-by-side comparisons, plants of the new *Echinacea* differed from plants of 'Kim's Knee High' in the following characteristics:

1. Plants of the new *Echinacea* were more compact than plants of 'Kim's Knee High'.
2. Plants of the new *Echinacea* had stronger peduncles than plants of 'Kim's Knee High'.
3. Plants of the new *Echinacea* were more freely branching than plants of 'Kim's Knee High'.
4. Plants of the new *Echinacea* and 'Kim's Knee High' differed in ray floret coloration as plants of 'Kim's Knee High' had pink-colored ray florets.

BRIEF DESCRIPTION OF THE PHOTOGRAPH

The accompanying photograph illustrates the overall appearance of the new *Echinacea.* The photograph shows the colors as true as it is reasonably possible to obtain in colored reproductions of this type. Colors in the photograph may differ slightly from the color values cited in the detailed botanical description which accurately describe the colors of the new *Echinacea.* The photograph comprises a side perspective view of a typical flowering plant of 'Polar Breeze' grown in an outdoor nursery.

DETAILED BOTANICAL DESCRIPTION

The aforementioned photograph and following observations and measurements describe plants grown in Mijdrecht, The Netherlands during the summer in an outdoor nursery and under conditions and practices which approximate those generally used in commercial *Echinacea* production. During the production of the plants, day temperatures ranged from 12° C. to 30° C. and night temperatures ranged from 5° C. to 15° C. Measurements and numerical values represent averages for typical flowering plants. Plants were two years old when the photograph and description were taken. In the following description, color references are made to The Royal Horticultural Society Colour Chart, 2001 Edition, except where general terms of ordinary dictionary significance are used.

Botanical classification: *Echinacea purpurea* 'Polar Breeze'.

Parentage: Naturally-occurring whole plant mutation of *Echinacea purpurea* 'Mistral', disclosed in U.S. Plant Pat. No. 20,498.

Propagation:

*Type.*—By micropropagation.

*Time to initiate roots.*—About six weeks at 13° C.

*Time to produce a rooted young plant.*—About six months at 18° C.

*Root description.*—Medium in thickness, fibrous; light brown in color.

*Rooting habit.*—Freely branching; dense.

Plant description:

*Plant form/growth habit.*—Upright and compact plant habit; inverted triangle; freely basal branching with about seven basal branches developing per plant; moderately vigorous growth habit.

*Plant height.*—About 36.8 cm.

*Plant diameter or spread.*—About 50 cm.

*Basal branches.*—Length: About 24.1 cm. Diameter: About 7 mm. Internode length: About 3.5 cm. Strength: Strong. Texture: Densely pubescent. Color: Close to 144B; towards the base, close to 144A.

Foliage description:

*Arrangement.*—Alternate, simple.

*Length.*—About 11.5 cm.

*Width.*—About 4 cm.

*Shape.*—Narrowly ovate to lanceolate.

*Apex.*—Acute.

*Base.*—Attenuate.

*Margin.*—Entire; undulate.

*Texture, upper and lower surfaces.*—Pubescent; rough.

*Venation pattern.*—Pinnate.

*Color.*—Developing leaves, upper surface: Close to 137B. Developing leaves, lower surface: Close to 137C. Fully expanded leaves, upper surface: Close to 137A to 137B; venation, close to 150D. Fully expanded leaves, lower surface: Close to 147B; venation, close to 145C.

*Petioles.*—Length: About 3.8 cm. Diameter: About 6 mm. Texture, upper and lower surfaces: Smooth; towards the edges, sparsely pubescent. Color, upper surface: Close to 145B; towards the edges, close to 141A. Color, lower surface: Close to 145A; towards the edges, close to 144A.

Inflorescence description:

*Appearance.*—Rotate anemone-type inflorescence form with ray and disc florets arranged acropetally on a capitulum; inflorescences positioned above the foliage on strong and thick peduncles facing upright.

*Quantity of inflorescences per plant.*—Freely flowering habit with about 16 inflorescences develop per flowering stem.

*Fragrance.*—Faint, sweet.

*Time to flower.*—Plants flower continuously from early July to mid-September in The Netherlands.

*Inflorescence longevity.*—Inflorescences maintain good substance for about two weeks on the plant; inflorescences not persistent.

*Inflorescence bud.*—Height: About 2.6 cm. Diameter: About 1.9 cm. Shape: Flattened globular. Color: Close to 143D.

*Inflorescence size.*—Diameter: About 6.5 cm. Depth (height): About 4.3 cm. Disc diameter: About 1.2 cm. Receptacle height: About 8 mm. Receptacle diameter: About 6 mm. Receptacle color: Close to 155A.

*Ray florets.*—Length: About 3.5 cm. Width: About 1.2 cm. Shape: Oblanceolate. Apex: Emarginate to praemorse. Base: Cuneate. Margin: Entire. Texture, upper and lower surfaces: Smooth, glabrous; longitudinally ridged. Number of ray florets per inflorescence: About 13 arranged in a single whorl. Aspect: Horizontal to reflexing. Color: When opening and fully opened, upper surface: Close to N155D. When opening and fully opened, lower surface: Close to N155D; occasionally toward the apex tinged with between 144A and 146A.

*Disc florets.*—Length: About 7.5 mm. Diameter: About 2 mm. Shape: Tubular, enlarged; apices acute. Number of disc florets per inflorescence: About 320. Texture, upper and lower surfaces: Smooth, glabrous. Color: Immature, inner and outer surfaces: Close to 144C to 144D; towards the apex, close to 144B to 144C. Mature, inner and outer surfaces: Between N144A and 151A.

*Receptacle spines.*—Quantity: One per disc floret. Shape: Acicular. Apex: Acute. Base: Attenuate. Texture: Smooth, glabrous. Color: Apex: Close to N30A. Mid-section: Close to 24A. Base: Close to 144B.

*Involucral bracts.*—Quantity per inflorescence: About 40 in about three whorls. Length: About 7 mm. Width: About 1.5 mm. Shape: Lanceolate. Apex: Acute. Base: Cuneate. Margin: Entire. Texture, upper surface: Smooth, glabrous. Texture, lower surface: Densely pubescent. Color, upper surface: Close to 141A. Color, lower surface: Close to 137A; towards the base, close to 143D.

*Peduncles.*—Length, terminal peduncle: About 21.3 cm. Length, fourth peduncle: About 17.8 cm. Length, seventh peduncle: About 17.2 cm. Diameter: About 3 mm. Strength: Strong. Aspect: Upright. Texture: Pubescent. Color: Close to 144A to 144B.

*Reproductive organs.*—Androecium (present on ray and disc florets): Quantity per floret: About five. Filament length: About 2.5 mm. Filament color: Close to 145C. Anther shape: Oblong. Anther length: About 3 mm. Anther color: Close to N200A. Pollen amount: Moderate to abundant. Pollen color: Close to 17A. Gynoecium (present only on disc florets): Quantity per floret: One. Pistil length: About 6 mm. Stigma shape: Tapering. Stigma color: Close to 53A. Style length: About 4 mm. Style color: Close to 42D. Ovary color: Close to 145D. Fruits/seeds: Fruit and seed development have not been observed.

Disease/pest resistance: Plants of the new *Echinacea* have not been shown to be resistant to pathogens and pests common to *Echinacea*.

Garden performance: Plants of the new *Echinacea* have been observed to have good garden performance and to tolerate rain and wind. Plants of the new *Echinacea* tolerate high temperatures of about 35° C. and are winter hardy to USDA Hardiness Zones 3 to 4.

It is claimed:

1. A new and distinct *Echinacea* plant named 'Polar Breeze' as illustrated and described.

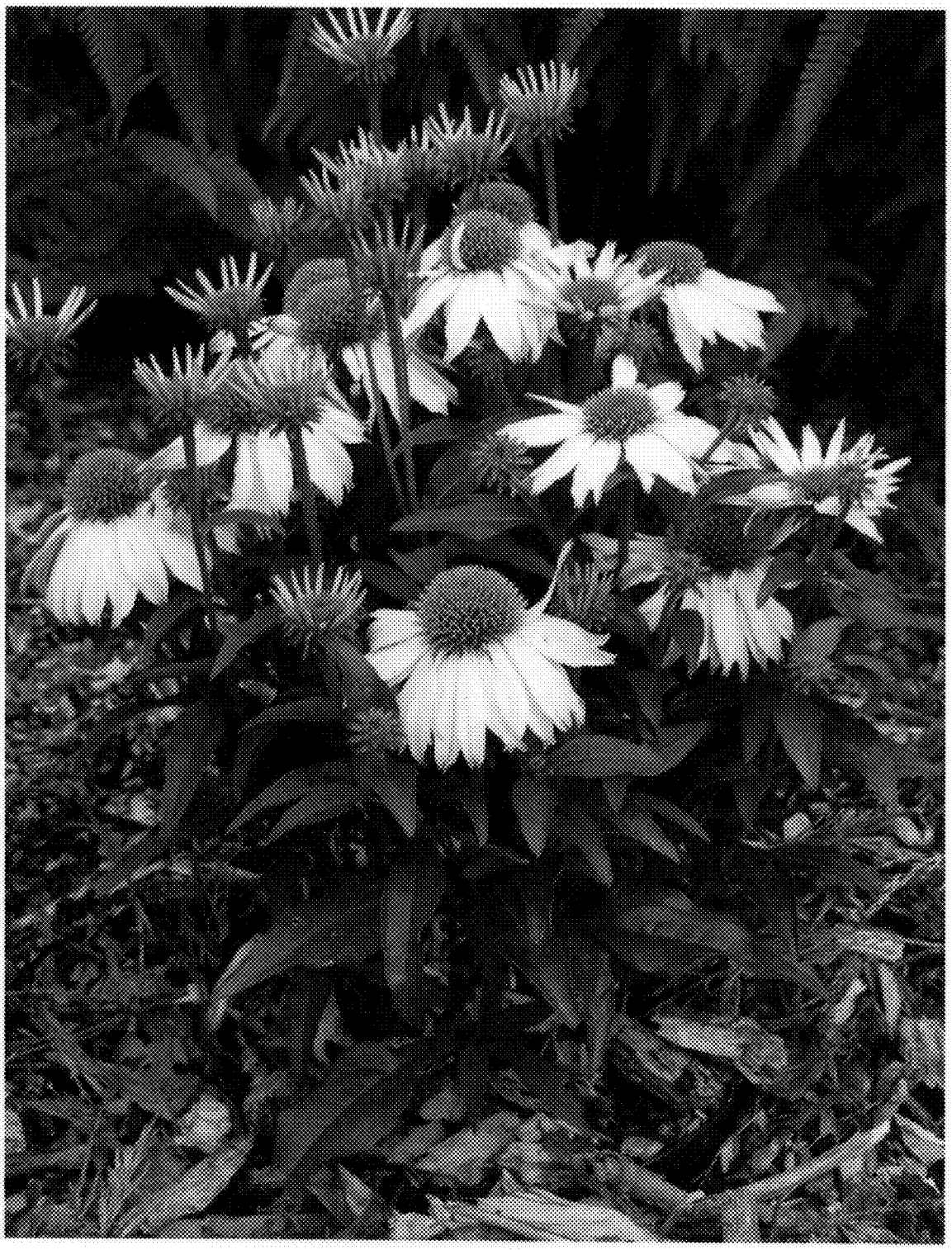

* * * * *